United States Patent [19]
Garbesi et al.

[11] Patent Number: 6,160,102
[45] Date of Patent: Dec. 12, 2000

[54] OLIGONUCLEOTIDE-ANTHRACYCLINE AND OLIGONUCLEOTIDE-ANTHRACYCLINONE CONJUGATES

[75] Inventors: Anna Maria Garbesi; Stefania Bonazzi, both of S. Lazzaro Di Savena; Stefania Zanella; Massimo Luigi Capobianco, both of Bologna; Giuseppe Giannini, Pomezia; Federico Arcamone, Nerviano, all of Italy

[73] Assignee: Consiglio Nazionale Delle Ricerche, Rome, Italy

[21] Appl. No.: 09/142,521

[22] PCT Filed: Mar. 12, 1997

[86] PCT No.: PCT/EP97/01246

§ 371 Date: Sep. 9, 1998

§ 102(e) Date: Sep. 9, 1998

[87] PCT Pub. No.: WO97/33897

PCT Pub. Date: Sep. 18, 1997

[51] Int. Cl.[7] .............................. C12Q 1/68; C07H 19/00; C07H 21/00; C07H 21/02; C07H 21/04; C07H 15/24

[52] U.S. Cl. ........................... 536/23.1; 435/6; 536/22.1; 536/6.4

[58] Field of Search ..................... 435/6, 91.1; 536/22.1, 536/23.1, 6.4

[56] References Cited

PUBLICATIONS

Biochimica et Biophysica Acta, 1049 (1990) 99–125, "Specific Regulation of Gene Expression by Antisense, Sense and Antigene Nucleic Acids", Claude Helene and Jean–Jacques Toulme.

Chemical Reviews, 1990, vol. 90, No. 4, "Antisense Oligonucleotides: A New Therapeutic Principle", Eugen Uhlmann and Anusch Peyman.

Angew. Chem. Int. Ed. Engl. 1993, 32, 666–690, "Sequence–Specific Recognition and Modification of Double–Helical DNA by Oligonucleotides", Nguyen T. Thuong and Claude Helene.

Nucleodies & Nucleotides, 10(103), 575–577 (1991), "Synthesis and Properties of Daunomycin Mono– and Oligonucleotide Derivatives", Zarytova V.F., Godovikova T.S., Maltseva T.V. Sergeyev D.S.

Tetrahedron, vol. 48, No. 7, pp. 1233–1254, 1992, "Solid–Phase Preparation of 5',3'–Heterobifunctional Oligodoxyribonucleotides Using Modified Solid Supports", Ulysse Asseline et al.

Molecular Basis of Specificity in Nucleic Acid–Drug Interactions, 275–290, 1990, "Design of Bifuctional Nucleic Acid Ligands", T. Montenay–Garestier et al.

*Primary Examiner*—Jezia Riley
*Attorney, Agent, or Firm*—Hedman, Gibson & Costigan, P.C.

[57] ABSTRACT

The present invention refers to conjugates formed by a natural or modified oligonucleotide, capable of forming a triple helix with a DNA chain, linked to the aglycone moiety of an anthracycline or to an anthracyclinone via an appropriated linker; such conjugates are capable to bind selectively to specific DNA regions inhibiting their transcription and therefore the formation of the corresponding codified protein.

18 Claims, No Drawings

OLIGONUCLEOTIDE-ANTHRACYCLINE AND OLIGONUCLEOTIDE-ANTHRACYCLINONE CONJUGATES

The present application is the national stage filing of and claims priority to International Application No. PCT/EP97/01246, filed Mar. 12, 1997 and Italian Application Ser. No. FI96A000044, filed Mar. 13, 1996.

1. FIELD OF THE INVENTION

The present invention refers to conjugates wherein a natural or modified oligonucleotide, capable of forming a specific triple-helix with a DNA-chain, is linked, via an appropriated linker, to the aglycone moiety of an anthracycline or to an anthracyclinone and to their use for the specific control of gene expression.

2. STATE OF THE ART

It is known [Claude Hélène et al. Biochimica et Biophysica Acta 1049, 99–125 (1990); Uhlmann E. et al., Chemical Reviews, 90, 543–584 (1990)] that synthetic oligonucleotides can be used for selectively inhibiting the expression of a gene by binding to the mRNA (antisense mechanism) or to the DNA (antigene mechanism). In the first case the oligonucleotide binds, via hydrogen bonds, to a Watson-Crick complementary sequence, present on the mRNA-target and interfers with the synthesis of the corresponding protein. In the second case the oligonucleotide recognises, and binds only to a polypurine:polypyrimidine region of double-stranded DNA. The synthetic oligomer, which places itself in the major groove of the DNA target, leads to the formation of a triple-helix segment via Hoogsteen or reverse-Hoogsteen hydrogen bonds with the purine strand. The presence of the triple-helix structure can interfere with the replication and transcription of the gene through various mechanisms. In order to have a permanent effect it is necessary that the structure of the triple-helix be thermodinamically stable. Such stability can be increased by an appropriate molecule (intercalator) added to one or both ends of the oligonucleotide [Nguyen T. Thuong et al. Angew. Chem. Int. Ed. Engl., 32, 666–690 (1993)]. Among the intercalating molecules daunorubicin was already investigated [V. F. Zarytova et al. Nucleosides and Nucleotides, 10, 575–577 (1991); U. Asseline et al. Tetrahedron, 48, 1233–1254 (1992)] but the results obtained are considered not satisfactory, since the increase in stability of the so obtained triple-helix complex is similar to that shown by other conjugates already studied [T.Montaney-Garestier et al. in Molecular Basis of Specificity in Nucleic Acid-Drug Interaction, Kluver Academic Publishers, p. 275–290, Nederlands (1990)]. It is therefore clear the interest of new conjugates with molecular residue that impart a higher stability to the triple-helix structures they form.

DETAILED DESCRIPTION OF THE INVENTION

The present invention refers to new conjugates wherein a natural or synthetically modified oligonucleotide, capable of forming a stable triple-helix with specific DNA-regions, is covalently bound through an appropriated linker, to the aglycone moiety of an anthracycline or to an anthracyclinone. Surprisingly, this particular way of connecting the oligonucleotide to the intercalator is very efficient for obtaining the desired results, i.e. a higher stability compared to that of conjugates described in the art.

Oligonucleotides capable of forming a triple-helix with a DNA-chain are known and are described, for example, in: Nguyen T. Thuong et al. Angew, Chem. Int. Ed. Engl., 32, 666–690 (1993).

Among the oligonucleotides, according to the present invention the oligodeoxynucleotides (ODN) are preferred. In particular according to the invention the following ODN can be used:

5'd($T_3CT_2CT_2CT_2$); SEQ ID NO.:1
5'd($T_2GTG_2TG_2T_2GTG_2$); SEQ ID NO.:2
5'd($GAGA_6(GA)_3$); SEQ ID NO.:3
5'd($T_3C^{5Me}T_2C^{5Me}T_2C^{5Me}T_2$); SEQ ID NO.:4
5'd($TC^{5Me}{}_3T_6C^{5Me}TC^{5Me}$); SEQ ID NO.:5
5'd($TGTGT_5GT_3GT_2T_4GT_3$); SEQ ID NO.:6
5'd($T_4C^{5Me}T_4G_6$) SEQ ID NO.:7.

Also the linkers used according to the present invention are the linkers commonly used in this field [see, for example: Nguyen T. Thuong et al. Angew. Chem. Int. Ed. Engl., 32, 666–690 (1993); D. J. Kessler et al. Nucleic Acids Res., 21, 4810–4815 (1993)].

In particular the following linkers were used:

—$(CH_2)_n$—, —$(CH_2$—$CH_2$—$O)_m$—, —$(CH_2$—$CH_2$—$CH_2$—$O)_p$—, $[(CH_2)_{2\text{-}5}$—$NH]_q$—, $[(CH_2)_{2\text{-}5}$—$S(O)_2]_q$— wherein n is an integer from 4 to 30, p is an integer from 1 to 6, m and q, same or different, are an integer from 2 to 9.

Among useful anthracyclines, according to the invention, are, for example, the natural or synthetic anthracyclines having a free OH-group in position 4 and/or 6. In particular: daunorubicin, doxorubicin, carminomycin (or the corresponding aglycones), the corresponding 5-imino derivatives and the corresponding 3'-alfa-cyanomorpholinyl derivatives.

According to a particular embodiment of the invention the oligonucleotide is bound, via the linker, to the D-ring of the anthracycline or of the aglycone, as for instance at position 4. According to another particular embodiment of the invention the oligonucleotide is linked to the B-ring of the aglycone, as for instance at position 6. The invention refers also to conjugates wherein the oligonucleotide capable of forming a triple-helix with a DNA chain is bound, via two linkers placed at its opposite ends, to two anthracycline molecules (on the aglycone moieties) or to two anthracyclinone molecules, such anthracyclines or anthracyclinones being same or different. Examples of conjugates according to the invention are schematically represented by Formula A:

(A)

$$X-Y-S-\overset{\overset{\displaystyle O}{\|}}{\underset{\underset{\displaystyle O^-}{|}}{P}}-O-ODN$$

wherein:

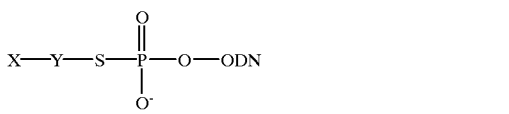

| | |
|---|---|
| Y = —$(CH_2)_6$— | |
| —$(CH_2)_{12}$— | |
| —$(CH_2CH_2OHCH_2CH_2)$— | |
| —$(CH_2CH_2NHCH_2CH_2)$— | |
| ODN = 5'd($T_3CT_2CT_2CT_2$); | SEQ ID NO.:1 |
| 5'd($T_2GTG_2TG_2T_2GTG_2$; | SEQ ID NO.:2 |
| 5'd($GAGA_6(GA)_3$); | SEQ ID NO.:3 |
| 5'd($T_3C^{5Me}T_2C^{5Me}T_2C^{5Me}T_2$; | SEQ ID NO.:4 |
| 5'd($TC_3{}^{5Me}T_6C^{5Me}TC^{5Me}$); | SEQ ID NO.:5 |
| 5'd($TGTGT_5GT_3GT_2T_4GT_3$); | SEQ ID NO.:6 |
| 5'd($T_4C^{5Me}T_4G_6$; | SEQ ID NO.:7 |

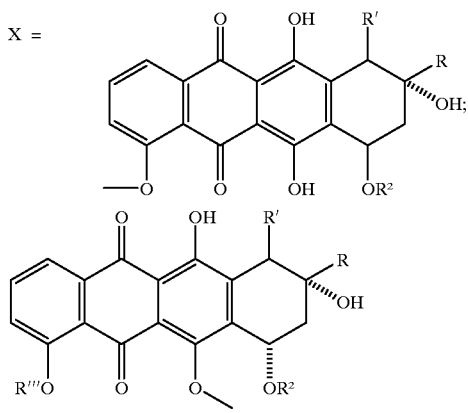

Wherein:
R=COCH$_3$, COCH$_2$OH, COCH$_2$OAc, C$_2$H$_5$; R'=H, OH, COOCH$_3$; R"=H, daunosamin; R'"=H, CH$_3$ The conjugates according to the invention are prepared, for example, following the hereinafter reported process.

First of all the halo-derivatives of the corresponding anthracyclinone or anthracycline are prepared (see also Scheme 1).

Aglycone 1, obtained in high yields by known techniques, is treated with an excess of 1,6-diiodohexane in refluxing chloroform in the presence of silver oxide. Column chromatography of the obtained crude product allows the separation of the corresponding omega-iodohexamethylene derivatives 2 and 3. Compound 3 is easily glycosylated with the protected sugar 4 in the presence of trimethylsilyltriflate giving compound 5. According to the invention, the oligonucleotides are prepared by solid phase synthesis in an automatic synthesizer (Pharmacia) using phosphoramidites, in order to obtain the corresponding 5'-thiophosphate derivatives. Coupling yields of about 96% are usually obtained. After deprotection, the oligonucleotides are purified by ion-exchange preparative chromatography. The fractions are analysed by ion-exchange HPLC. The fractions having a purity higher than 90% are transformed into the correspondig sodium salt and lyophilized. The above said halo-derivatives 2, 3, and 5 are then allowed to react with the sodium salt of the 5'-thiophosphate oligonucleotide in the presence of 15-crown-5 in DMF/H$_2$O giving the wanted final conjugates which are purified by HPLC (see Scheme 2).

EXAMPLE 1

O-alkylation of carminomycinone

To a solution of carminomycinone [compound of formula (1) wherein: R=CO—CH$_3$ e R'=H] (2.64 g; 6.9 mmol) in anhydrous CHCl$_3$ (400 ml) 1,6-diiodohexane (16.88 g; 50 mmol) and Ag$_2$O (2.5 g; 11 mmol) are added under stirring. The mixture is refluxed for 4 days, the decrease of the starting product is checked by TLC (CH$_2$Cl$_2$/acetone 98:2) and Ag$_2$O (7 mmol) is added on the third and fourth day. At the end the mixture is filtered on paper filter, at room temperature, in order to remove the silver salts and the solvent is eliminated under reduced pressure. The residue is treated with pentane, in order to separate the unreacted haloderivative and the so obtained crude product is subjected to chromatography on silica gel (CH$_2$Cl$_2$/acetone 98:2). Two solid products are obtained: one is red (620 mg) and the other is yellow (579 mg); their structure was determined by mass spectrometry and $^1$H and $^{13}$C-NMR. The red product is 4-dimethoxy-4-O-(6-iodohexyl)-carminomycinone, while the yellow product is 4-dimethoxy-6-O-(6-iodohexyl)-carminomycinone.

EXAMPLE 2

Glycosidation

To a mixture of 4-dimethoxy-4-O-(6-iodohexyl)-carminomycinone (obtained according to Example 1) (270 mg; 0.454 mmol) and N-allyloxy-1,4-bis-(4-nitro-benzoyl)-daunosamin (obtained according to known techniques) (541 mg; 1.01 mmol) molecular sieves 4 A (2.8 gr), treated at the flame, are added under anhydrous conditions; thereafter CH$_2$Cl$_2$ (90 ml), Et$_2$O (23 ml) and trimethylsilyltriflate (0.38 ml), at −5° C., are also added to the mixture. After 15' the reaction is completed. At 0° C. a 1% solution of sodium bicarbonate (25 ml) is added and the mixture is diluted with CH$_2$Cl$_2$ and therafter extracted with the same solvent. The organic fractions are washed with 1% bicarbonate then with water up to neutrality. From the organic phase, after anhydrification and evaporation of the solvent, the crude protected 4-demethoxy-4-O-(6-iodohexyl)daunomicin is obtained (330 mg).

EXAMPLE 3

Deprotection

The product according to Example 2 (330 mg) is dissolved in methanol (144 ml) and methylene chloride; the solution is cooled at −5° C. and a 0.5 M (1.8 ml) of K$_2$CO$_3$ solution is added. The reaction course is checked by TLC (CHCl$_3$/iPrOH 95:5) and is completed in 1 h. The reaction mixture is added with 0.05 N HCl up to colour change from violet to orange, concentrated under reduced pressure at low temperature and finally added with CH$_2$Cl$_2$. The organic solution is washed with water and dried, the solvent is removed under reduced pressure. The residue is dissolved in 50 ml of anhydrous CH$_2$Cl$_2$ and Ph$_3$P (8.25 mg; 0.0315 mmol), Pd(O)-tetrakis (11 mg, 0.0095 mmol) and 2-methyl-butyric acid (80 mg; 0.78 mmol) are added. The reaction is performed in the dark and the reaction course is cheked by TLC (CHCl$_3$/MeOH/HCOOH/H$_2$O 65:7.5:1.5:0.5). At the end, the reaction mixture is diluted with CH$_2$Cl$_2$, washed with NaHCO$_3$ and H$_2$O, dried and evaporated. The crude product, 4-dimethoxy-4-O-(6-iodohexyl) daunomycin is purified by preparative HPLC. The identity of the purified product is confirmed by mass spectrometry (FAB MS$^+$ 724).

EXAMPLE 4

Synthesis of the 5'-phosphorothioate oligodeoxynucleotide ps$^5$'-TTT CTT CTT CTT (ODN)

The synthesis is performed with an automatic synthesizer using the "phosphoroamidite" method. At the end of the ODN growth phase, after detritylation, a mixture of 0.1 M N,N-diisopropyl-(bis)cyanoethyl phosphite in CH$_3$CN (100 μl) and 0.5 M tetrazole in CH$_3$CN (150 μl) is recycled in the reaction column for 7 min., flux 1 ml/min (three times). After washing with CH$_3$CN the thio-oxydation reaction with sulfur is performed using a solution 0.1 M solution in CH$_3$CN of Beaucage reagent which is passed through the reaction column for 40 sec., flux 1 ml/min. At the end of the synthesis the ODN linked to the solid substrate is treated with 28% NH$_3$ at 50° C. for 24 h. The crude product is purified by preparative ion-exchange chromatography (column h=12 cm; diam.=2 cm) and the fractions containing the product are analyzed by ion-exchange HPLC. The fractions having a purity higher than 90% are pooled, transformed into the corresponding sodium salt by a DOWEX 50 WX 8$^R$ resin, repeatedly treated with CHELEX$^R$ resin to eliminate possible residues of bivalent metals, and lyophilized. The so obtained 5'-thiophosphate oligodeoxynucleotide is characterized, in respect to the unreacted ODN, by TLC, $^{31}$P NMR, electronspray mass spectrometry.

EXAMPLE 5

Synthesis of conjugate (8)

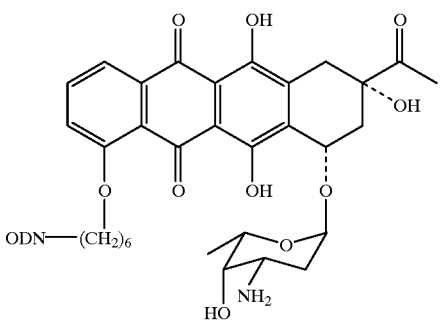

To the sodium salt of the ODN obtained in Example 4 above (0.1 μmol) dissolved in DMF (125 μl) and H$_2$O (50 μl), in the presence of 15 -crown-5 (13 μl), 1 mg of 4-demethoxy-4-O-(6-iodohexyl)daunomycin is added. The reaction mixture is left at 50° C., checking the formation of the conjugate by reverse-phase HPLC. When the starting ODN is completely consumed the excess anthracycline is eliminated by column chromatography using reverse-phase silica gel RP-18. The crude conjugate is purified by reverse-phase HPLC and characterized by HPLC, UV and fluorescence spectroscopy. Analogously, the following products are obtained:

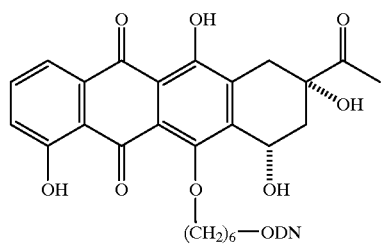
(6)

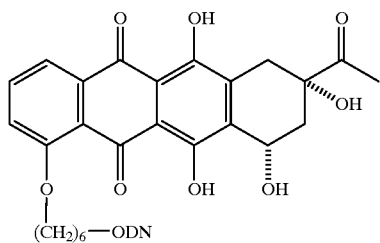
(7)

Binding tests

The affinity of the conjugates according to the invention for the target sequence in double strands (B):

5'AGGACGAAAGAAGAAGAACTTT

3'TCCTGCTTTCTTCTTCTTGAAA        (B)

is determined by UV and fluorescence spectroscopy. Since in the ODN forming triple-helix unmethylated cytidines are present, its binding strenght is a function of pH, therefore the stability of the triple-helical complexes is measured at pH 5.5; 6.5; 6.8. Thermal stability values of the triple-helical complexes formed by target (B) and conjugates 6–8 (above described), conjugate 9

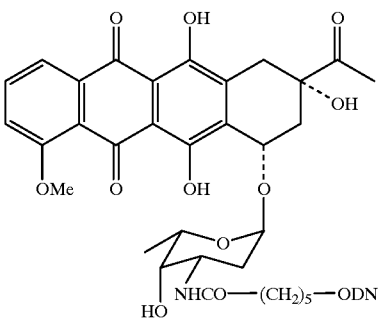
(9)

(prepared as described by Asseline, U. et al. in Tetrahedron, 43, 1233–1254 (1992)), and the non-derivatized oligodeoxynucleotide (10) are compared.

OH-TTT CTT CTT CTT        (10)

The dissociation is monitored measuring the variation of the absorbance at 260 nm with increasing temperature. From the melting curves, obtained by plotting the absorbance values at the various temperatures, the Tm (temperature of 50% dissociation of the triple helix into double helix target and single strand) values reported in TABLE 1 are obtained. The triple-helix formation between the above said ligands and the DNA-target (B) is confirmed by gel electrophoresis at 15° C., pH 5.5. The collected data show that, at all investigated pH values, the presence of a daunomycin-derivative covalently linked, via the hexamethylene linker, at the 5' extremity of the dodecamer gives rise to complexes which are much more stable (with the exception of 9) than those formed by the underivatized ODN (10). The increase in thermal stability of the triple-helix due to the anthracycline chromophores is high and similar for all the conjugates 6–8. On the contrary conjugate 9 forms a much less stable complex. This difference is particularly evident at pH 6.8, where the contribution of the ODN to the complex stability is very low; at 20° C., while the triple-helices formed by conjugates 6–8 are largely undissociated, the one formed by conjugate 9 is almost completely denatured. The fact that the higher stability of the complexes formed by the conjugates according to the present invention is due to the intercalation of the aglycone moiety in the DNA-target is confimed by spectrofluorometric measurements. It is in fact known that the fluorescence of anthracyclines is lowered by their intercalation between DNA base pairs. The fluorescence intensity at 590 nm of the triple-helix complex at pH 5.5 is measured at 25° C. and compared to that obtained at the same temperature after increasing the pH to 8.2, a condition that is not compatible with the existence of triple-helix involving cytidines in the third strand. The fluorescence measured at pH 8.2 is considerably higher (about three times) than that measured at acid pHs and comparable to that obtained at the same pH in the absence of the double-helical DNA target. These results show that the strong affinity for the double stranded DNA of the conjugates according to the invention is a consequence of the intercalation of the anthracycline chromophore in the triple-helix complex. The behaviour of the conjugates according to the invention as bifunctional ligands of DNA is confirmed by the fact that the intercalating moiety does not remain intercalated at pH values which are not compatible with the binding-characteristics of the oligopyrimidine chain. It is therefore evident that the conjugates obtained according to the invention represent products capable of forming more stable sequence specific complexes, as required by the antigene technology, with the target nucleic acid. It is also important to note that the binding of an oligonucleotide (through a covalent bond of the type present in the herein described conjugates) to a molecule capable of performing its action when intercalated in the DNA double helix (as for example antitumor anthracyclines agents) allows to direct the above said activity on specific regions of the genome.

This selective attack allows to hit only the genes which are causative of disease. As the site of action of the new products is on DNA, that is also the main cell target of these antitumor agents, the conjugates according to the invention are useful to specifically direct these drugs against the activated oncogenes and against the proviral genome of a retrovirus, integrated in the host DNA. They represent therefore an efficient way to direct cytotoxic drug selectively on the target because of their stable complexation to the DNA in the specific region.

TABLE 1

| compounds | Tm (temperature of 50% dissociation) | | |
|---|---|---|---|
| | pH 5.5 | pH 6.5 | pH 6.8 |
| 6 | 55° C. | 43° C. | 31° C. |
| 7 | 51° C. | 35° C. | 27° C. |
| 8 | 55° C. | 45° C. | 36° C. |
| 9 | 45° C. | 25° C. | 16° C. |
| 10 | 41° C. | 23° C. | 13° C. | wherein:

a=I—$(CH_2)_6$—I/$Ag_2O$ b=TMSOTf/$CH_2Cl_2$/$Et_2O$ c=$K_2CO_3$ 0.5 M/MeOH d=Pd$(Ph_3P)_4$/2-methylbutyric acid R=$COCH_3$, $COCH_2OH$, $COCH_2OAc$, $C_2H_5$

R'=H, OH, $COOCH_3$

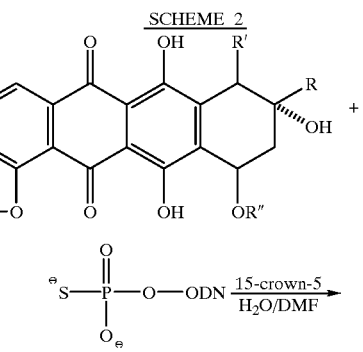

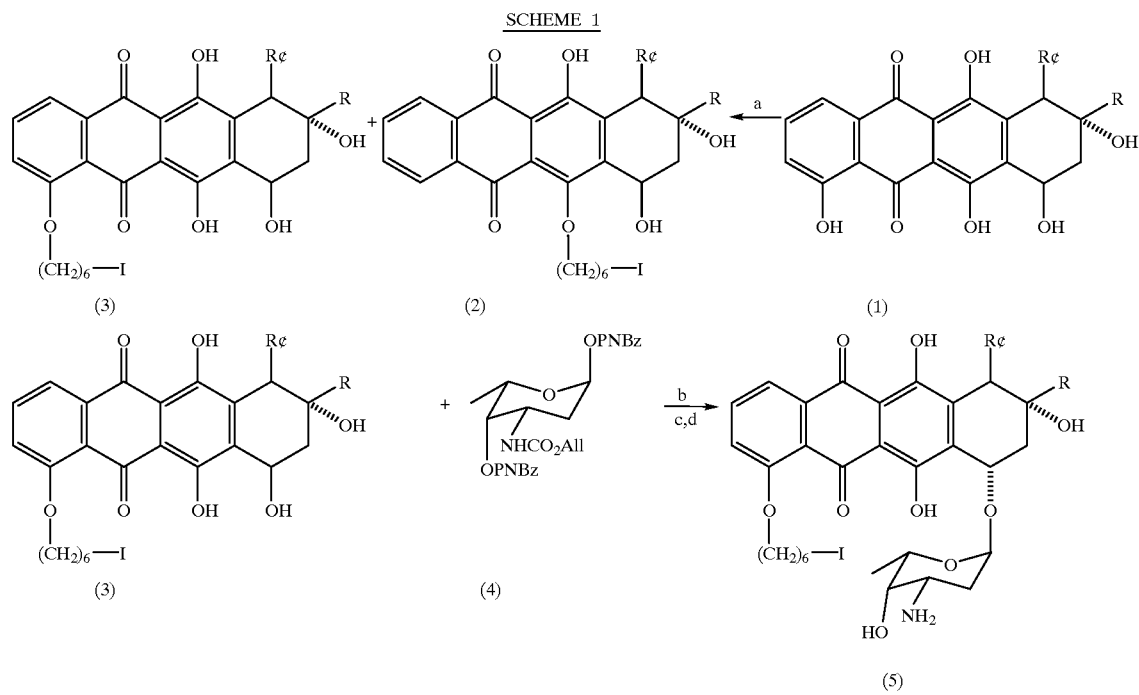

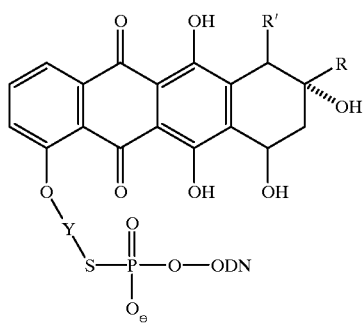

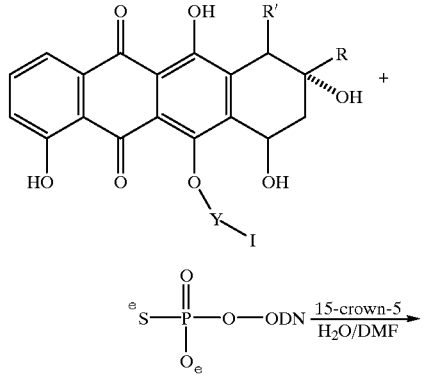

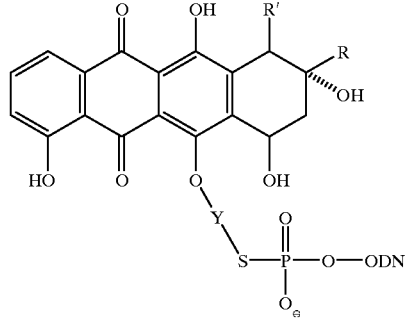

wherein:

| | |
|---|---|
| Y = —(CH$_2$)$_6$— | |
| —(CH$_2$)$_{12}$— | |
| —(CH$_2$CH$_2$OHCH$_2$CH$_2$)— | |
| —(CH$_2$CH$_2$NHCH$_2$CH$_2$)— | |
| ODN = 5'g(T$_3$CT$_2$CT$_2$CT$_2$); | SEQ ID NO.:1 |
| 5'd(T$_2$GTG$_2$TG$_2$T$_2$GTG$_2$; | SEQ ID NO.:2 |
| 5'd(GAGA$_6$)GA($_3$); | SEQ ID NO.:3 |
| 5'd(T$_3$C$^{5Me}$T$_2$C$^{5Me}$T$_2$C$^{5Me}$T$_2$; | SEQ ID NO.:4 |
| 5'd(TC$_3$$^{5Me}$T$_6$C$^{5Me}$TC$^{5Me}$); | SEQ ID NO.:5 |
| 5'd(TGTGT$_5$GT$_3$GT$_2$T$_4$GT$_3$); | SEQ ID NO.:6 |
| 5'd(T$_4$C$^{5Me}$T$_4$G$_6$; | SEQ ID NO.:7 |

---

What is claimed is:

1. Conjugates consisting of a natural or modified oligonucleotide capable of forming a triple-helix complex with a double stranded DNA, linked via an appropriate linker, to the aglycone-moiety of an anthracycline or to an anthracyclinone.

2. Conjugates according to claim 1, wherein the oligonucleotide is linked via the linker, to the D-ring of the anthracycline or the anthracyclinone.

3. Conjugates according to claim 2 wherein the oligonucleotide is linked to the D-ring in position 4.

4. Conjugates according to claim 1, wherein the oligonucleotide is linked to the B-ring of the anthracycline or the anthracyclinone.

5. Conjugates according to claim 4 wherein the oligonucleotide is linked to the B-ring in position 6.

6. Conjugates according to claim 1 wherein the oligonucleotide is a oligodeoxynucleotide.

7. Conjugates according to claim 6 wherein the oligonucleotide capable of forming a triple-helix is chosen from the group consisting of: 5'd($T_3CT_2CT_2CT_2$); 5'd($T_2GTG_2TG_2T_2GTG_2$); 5'd($GAGA_6(GA)_3$); 5'd($TGTGT_5GT_3GT_2T_4GT_3$); 5'd($TC^{5Me}{}_3T_6C^{5Me}TC^{5Me}$); 5'd($T_3C^{5Me}T_2C^{5Me}T_2C^{5Me}T_2$); 5'd($T_4C^{5Me}T_4G_6$).

8. Conjugates according to claim 1 wherein the linker is chosen from the group consisting of: —$(CH_2)_n$—, —$(CH_2$—$CH_2$—$O)_m$—, —$(CH_2$—$CH_2$—$CH_2$—$O)_p$—, —$[(CH_2)_{2-5}$—$NH]_q$—, $[(CH_2)_{2-5}$—$S(O)_2]_q$ wherein n is an integer 4 to 30, p is an integer from 1 to 6, m and q, same or different, are an integer from 2 to 9.

9. Conjugates according to claim 1 wherein the anthracycline is an anthracycline having a free OH-group in position 4 and/or 6.

10. Conjugates according to claim 9 wherein the anthracycline is chosen from the group consisting of: daunorubicin, doxorubicin, carminomycin, or the corresponding anthracyclinone, the corresponding 5-imino derivatives or the corresponding 3'-alfa-cyanomorpholinyl derivatives.

11. Conjugates according to claim 2 wherein the aglycone is the aglycone of an anthracycline according to claim 8.

12. Conjugates according to claim 2 wherein the aglycone is the aglycone of an anthracycline according to claim 10.

13. Conjugates according to claim 1 wherein the oligonucleotide capable of forming a triple-helix is linked, via two linkers placed at its opposed ends, to two anthracyclines molecules (on the aglycones moieties) or to two anthracyclinone molecules, such anthracyclines or anthracyclinones being same or different.

14. Conjugates according to claim 1, schematically represented by formula A:

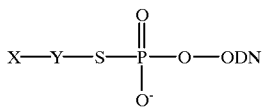

(A)

wherein:

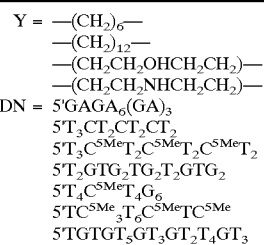

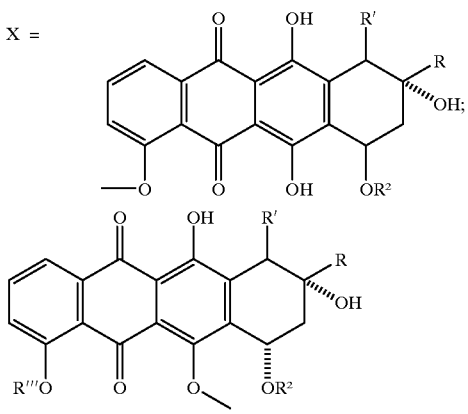

wherein:

R=$COCH_3$, $COCH_2OH$, $COCH_2OAc$, $C_2H_5$; R'=H, OH, $COOCH_3$; R"=H, daunosamin; R'''=H, $CH_3$.

15. Compound of the general formula (2):

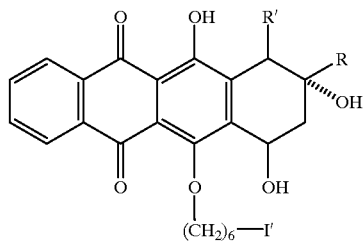

(2)

wherein R=COCH₃, COCH₂OH, COCH₂OAc, C₂H₅; and R'=H, OH, COOCH₃.

16. Compound of the general formula (3):

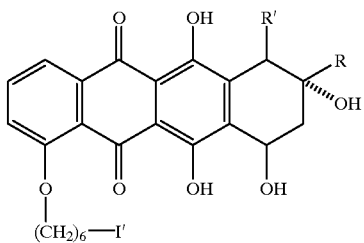

(3)

wherein R=COCH₃, COCH₂OH, COCH₂OAc, C₂H₅; and R'=H, OH, COOCH₃.

17. Compound of the general formula (5):

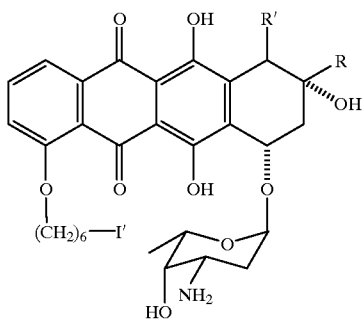

(5)

wherein R=COCH₃, COCH₂OH, COCH₂OAc, C₂H₅; and R'=H, OH COOCH₃.

18. Conjugates consisting of a natural or modified oligonucleotide according to claim 1 which are capable of forming a triple-helix complex with a double stranded DNA, linked via an appropriate linker selected from the group consisting of —(CH₂)—, —(CH₂—CH₂O)$_q$, —(CH₂—CH₂—CH₂—O)$_p$, —[(CH₂)$_{2-5}$—NH]$_q$, [(CH₂)$_{2-5}$—S(O)₂]$_q$ wherein n is an integer of 4 to 30, p is an integer from 1 to 6, m and q are the same or different and are an integer from 2 to 9 to the aglycone-moiety of an anthracycline or to an anthracyclinone.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (iii) HYPOTHETICAL: NO (xi) SEQUENCE DESCRIPTION: SEQ ID NO: 1:

TTTCTTCTTC TT                        12

(2) INFORMATION FOR SEQ ID NO: 2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (iii) HYPOTHETICAL: NO (xi) SEQUENCE DESCRIPTION: SEQ ID NO: 2:

TTGTGGTGGT TGTGG                    15

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO: 3:

GAGAAAAAAG AGAGA                                                  15

(2) INFORMATION FOR SEQ ID NO: 4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Bases C at positions 4, 7, 10
            are methylated (xi) SEQUENCE DESCRIPTION: SEQ ID NO: 4:

TTTCTTCTTC TT                                                        12

(2) INFORMATION FOR SEQ ID NO: 5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Bases at positions 2, 4, 6, 13
            and 15 are methylated (xi) SEQUENCE DESCRIPTION: SEQ ID NO: 5:

TCTCTCTTTT TTCTC                                                  15

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO: 6:

TGTGTTTTTG TTTGTTTTTT GTTT                                24

(2) INFORMATION FOR SEQ ID NO: 7:

-continued

```
    (i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (iii) HYPOTHETICAL: NO (ix) FEATURE:
         (D) OTHER INFORMATION: The base C at position 5 is methylated (xi) SEQUENCE DESCRIPTION: SEQ ID NO: 7:

TTTTCTTTTG GGGGG                                                      15
```